United States Patent
Schmidt et al.

(10) Patent No.: US 6,524,319 B1
(45) Date of Patent: Feb. 25, 2003

(54) SURGICAL INSTRUMENT FOR MECHANICALLY REMOVING BONE CEMENT

(75) Inventors: Joachim Schmidt, Bergisch Gladbach (DE); Thorsten Raabe, Salem-Buggensegel (DE); Wolfgang Merkle, Meersburg (DE)

(73) Assignee: Ferton Holding S.A., Delmont (CH)

( * ) Notice: Subject to any disclaimer, the term of this patent is extended or adjusted under 35 U.S.C. 154(b) by 0 days.

(21) Appl. No.: 09/868,768

(22) PCT Filed: Nov. 5, 1999

(86) PCT No.: PCT/EP99/08492

§ 371 (c)(1),
(2), (4) Date: Jun. 21, 2001

(87) PCT Pub. No.: WO00/36999

PCT Pub. Date: Jun. 29, 2000

(30) Foreign Application Priority Data

Dec. 22, 1998 (DE) .......................................... 198 59 412

(51) Int. Cl.[7] .................................................. A61F 5/00
(52) U.S. Cl. ............................ 606/86; 606/80; 606/96; 606/99
(58) Field of Search .............................. 606/53, 79, 80, 606/86, 92–99, 180

(56) References Cited

U.S. PATENT DOCUMENTS

| 5,122,134 A | * | 6/1992 | Borzone et al. | ............ 606/180 |
| 5,192,283 A | * | 3/1993 | Ling et al. | ..................... 606/92 |
| 5,374,270 A | * | 12/1994 | McGuire et al. | ............. 606/86 |
| 5,895,389 A | * | 4/1999 | Schenk et al. | ................ 606/80 |

\* cited by examiner

*Primary Examiner*—Gregory Huson
*Assistant Examiner*—Tuan Nguyen
(74) *Attorney, Agent, or Firm*—Diller, Ramik & Wight

(57) ABSTRACT

For a surgical instrument for removing distal and/or peripheral cement (2) and/or a medullary block in a medullary cavity (8) when endoprostheses are replaced, the surgical instrument comprising a drilling tool (4) and an extraction tool (6), it is provided that the drilling tool (4) and the extraction tool (6) comprise a bore (14,16) extending coaxially to the respective tool shaft (12) for receiving a centering bolt (10), that the bore diameter of the coaxial bores (14,16) of the drilling tool (4) and the extraction tool (6) is substantially adapted to the diameter of the centering bolt (10), and that the centering bolt (10) anchored at a predetermined location in the cement (2) or the medullary block and the medullary space (5) located distally below it is configured as an axial guide for the drilling tool (4) and the extraction tool (6), respectively.

10 Claims, 3 Drawing Sheets

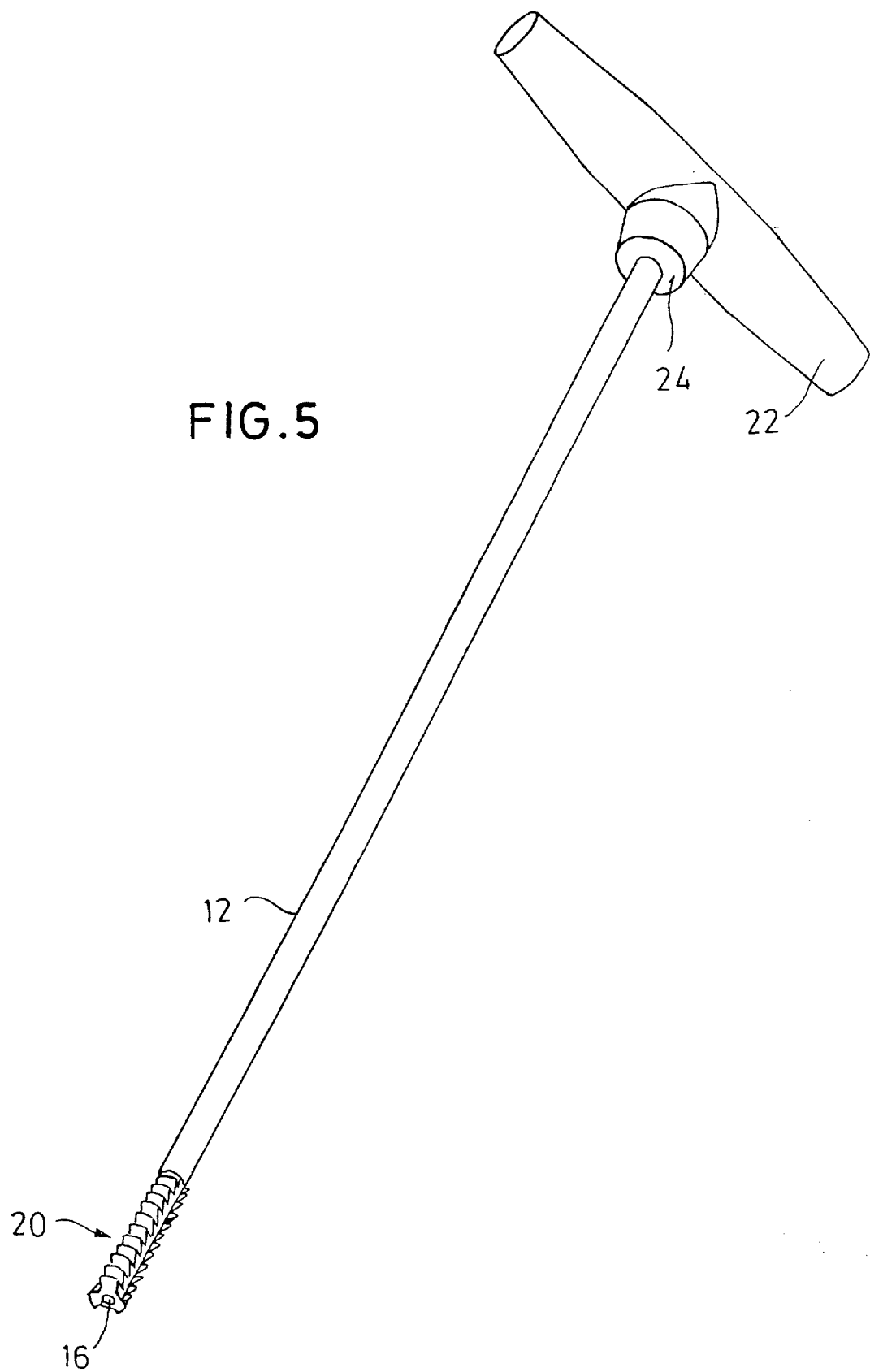

SURGICAL INSTRUMENT FOR MECHANICALLY REMOVING BONE CEMENT

BACKGROUND OF THE INVENTION

The invention relates tho a surgical instrument for mechanically removing bone cement according to the pre-characterizing part of claim 1.

Such surgical instruments are required for orthopaedic operations, e. g. for removing the remaining bone cement, e.g. of PMMA, after removal of an endoprosthesis (hip, knee, shoulder), and to allow perfect fit of the endoprosthesis to be newly set in.

For removing the cement e.g. chiselling tools are driven into the cement with the aid of a hammer to separate the cement from the bone in the medullary cavity.

Removal of the bone cement is preferably required in the field of orthopaedic surgery when loose or infected endoprostheses are to be replaced or removed.

The number of prosthesis replacements is continuously growing, in particular in the field of hip endoprosthetics. Removal of the bone cement used for prostheses fixed with cement is laborious and time-consuming. Hitherto the cement has normally been removed by means of chisels of different shapes, the safe employment of which is problematic e. g. due to poor visibility in the depth of the medullary cavity. Besides the high expenditure of time damage to the bone may occur, which would render new implantation of a prosthesis impossible or result in excessive loss of bone.

Extraction instruments are employed either without direct visual check or the position must be checked by means of X-ray image intensifiers. Malpositioning is possible and cannot be completely precluded even when X-ray image intensifiers are used for checking purposes. Malpositioning leads to damage of the bone which necessitates extended operations.

The employment of X-ray image intensifiers involves the risk of radiation exposure of the patient and the operation personnel. Known extraction instruments, in particular drills, lead, due to their configuration, to a forced pressure increase in the medullary cavity during penetration of the cement or the medullary block in peripheral direction, which may cause fat embolisation.

In the event of a hip joint replacement operation the cement used to fix the old prosthesis must be removed prior to setting in the new prosthesis. Since the thigh bone is a long tubular bone, the distal cement residue and the medullary block are difficult to access via the opening at the proximal end.

During the removal of the cement and/or the medullary block conventional tools produce a pressure increase in the bone below the medullary block. When work is carried out on the distal cement residue and the medullary block, respectively, a force is applied thereto. This may lead to compression of the space behind—an effect similar to that caused by an air pump—and result in a pressure increase due to which the abundant fat in the medullary space can be pressed into the blood stream. This leads to fat embolisms which frequently result in permanent injury of the patient and in many cases even to death. Investigations have shown that a fat embolism is possibly not covered by anaesthesia. Death occurs suddenly and unforeseen. Fat embolisms are particularly critical in the case of a sepsis since germs are pressed into the blood stream together with the fat such that the sepsis is transmitted.

SUMMARY OF THE INVENTION

It is an object of the invention to provide a surgical instrument for removing distal cement residues and medullary blocks, which can prevent malpositioning of the extraction tool and pressure increases in the medullary space.

According to the invention the drilling tool and the extraction tool preferably comprise a bore extending coaxially to the respective tool shaft for receiving a centering bolt, the bore diameter of the coaxial bores of the drilling tool and the extraction tool are substantially adapted to the diameter of the centering bolt, and the centering bolt anchored at a predetermined location in the cement or the medullary block and in the medullary space located distally below is configured as an axial guide for the drilling tool and the extraction tool, respectively.

An essential feature of said extraction tool is that at least the distal end of the extraction tool is configured as a cannula in its central portion. When cement is removed, a centering bolt is first inserted into the distal cement residue and/or the meduallary block. By means of a drill which is of cannular configuration at least at the distal end the cement residue and/or the medullary block is completely pierced, wherein the centering bolt is configured as an axial guide. After predrilling the extraction tool is inserted into the bore previously produced down to the distal end of the cement residue and/or the medullary block, wherein the remaining portion of the centering bolt is again configured as a guide. Then the operator pulls out the distal cement residue and/or medullary block. If the cement residue is firmly embedded in the bone cement and/or the medullary block, the operator may beat with a special hammer on a shoulder surface of the extraction tool thus knocking out the extraction tool together with the cement block or the medullary block.

The cannular configuration of the extraction tool presents the following advantages:

Since the centering bolt serves as a guide, exact positioning of the instrument point is possible despite difficult access in the long tubular bone and poor visibility. This prevents perforation or fissured fracture of the bone due to excursion of the extraction tool during predrilling of the bone and insertion of the extraction tool. Perforation or fissured fracture of the bone results in a slower healing process and may, in the worst case, render implantation of the new prosthesis impossible.

The coaxial bores are open at the proximal end thus forming a pressure compensation duct.

When using the drilling tool of cannular configuration and the extraction tool of cannular configuration, a pressure compensation via the axial bore takes place prior to and during removal of the cement residue and/or the medullary block, the pressure compensation preventing a pressure increase in the medullary space below the cement residue and/or the medullary block such that the risk of fat embolism or transmitted sepsis is reduced.

The extraction tool preferably comprises a self-cutting male thread which can be inserted at a low expenditure of force into the bore produced by the drilling tool.

The male thread is preferably configured as a cortex screw such that the male thread is anchored in the predrilled bore due to a self-locking effect. The coaxial bores provided in the extraction tool and the drilling tool for receiving the centering bolt have a diameter ranging from approximately 1.5 to 4 mm, preferably approximately 2–3 mm.

The centering bolt has a smaller diameter with respect to the coaxial bores of the drilling tool and the extraction tool.

This allows both the drilling tool and the extraction tool to be guided, with a clearance, by the same centering bolt such that exact positioning of the tools is possible.

The distal ends of the coaxial bores of the drilling tool and the extraction tool may be flared towards the outside. This flared configuration of the distal end of the bores facilitates insertion of the tools.

The coaxial bores provided in the drilling tool and/or the extraction tool may comprise a stop defining the maximum penetration depth of the tool. In this manner the tools can be prevented from being too deeply inserted into the distal medullary space and/or the cement residue or the medullary block.

BRIEF DESCRIPTION OF THE DRAWINGS

Hereunder an embodiment of the invention is explained in detail with reference to the drawings in which:

FIG. 5 shows a perspective view of the extraction tool.

DESCRIPTION OF THE PREFERRED EMBODIMENTS

Figure 1:
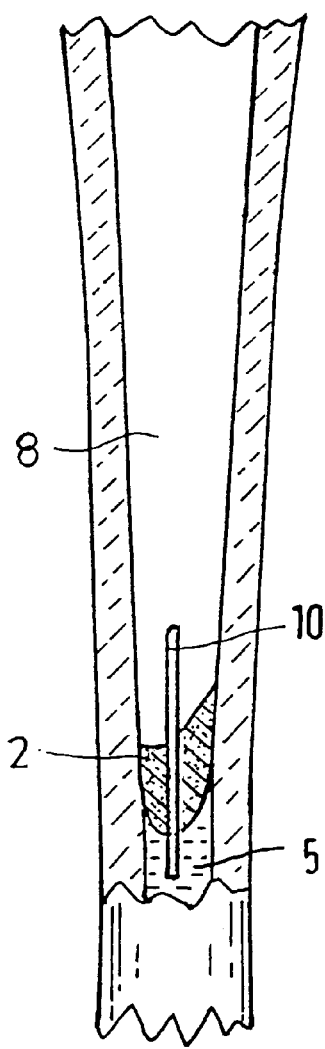
FIG. 1 shows a cross-section of the proximal end of a thigh bone after removal of the hip joint prosthesis.

FIG. 1 shows a cross-section of the proximal end of a thigh bone after removal of the hip joint prosthesis. The proximal peripheral cement residues 2 can be removed in a conventional manner by means of chisels. Conversely, removal of the cement and/or removal of a medullary block at the distal end of the medullary cavity 8 must be effected with the aid of an extraction tool 6. A medullary block of cement or bone material is used in the event of insertion of a prosthesis to close the medullary cavity towards the medullary space 5 located distally below it.

Figure 2:
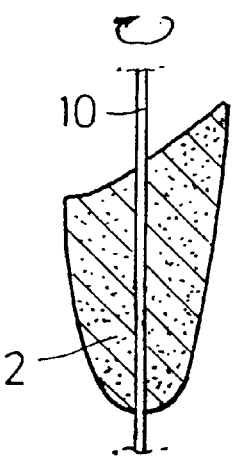
FIG. 2 shows insertion of the centering bolt.

FIG. 2 shows insertion of a centering bolt 10 through the cement residue 2 at the distal end of the medullary cavity 8 into the medullary space 5.

Under endoscopic or direct inspection first the centering bolt 10 is positioned at the desired location in the cement residue 2 or in the medullary block. On an inclined surface it may be necessary to punch the desired entry point in a suitable manner by means of a punching tool. The centering bolt 10 may be provided with a drilling point such that it can be easily inserted through the cement residue 2 into medullary space 5 located distally below the cement residue 2.

The centering bolt has a diameter of approximately 1.5 to 4 mm, preferably approximately 2.5 mm. It may further be provided with a male thread to improve anchoring of the centering bolt 10 in the cement residue 2 and the medullary space 5.

When the centering bolt 10 is fixed in the cement residue 2 and/or a medullary block and the medullary space 5, such that a portion of the centering bolt 10 proximally projects from the cement residue 2, as shown in FIG. 1, the centering bolt 10 may serve as a guide for a drilling tool 4 and an extraction tool 6.

Figure 3:
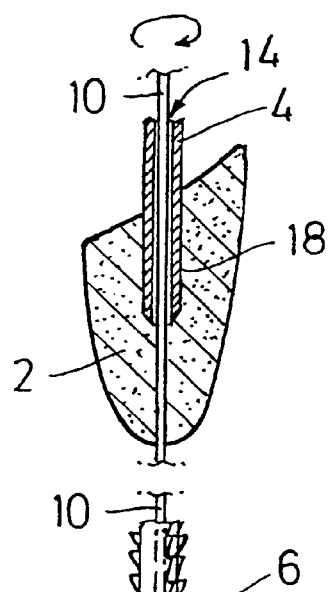
FIG. 3 shows guidance of the drilling tool by means of the centering bolt.
Figure 4:
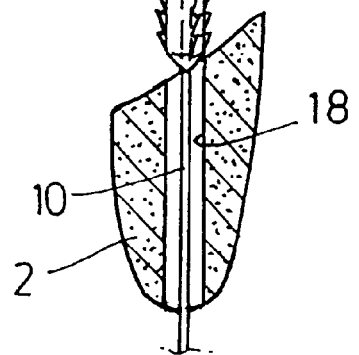
FIG. 4 shows guidance of the extraction tool by means of the centering bolt.

FIG. 3 shows the distal end of a drilling tool 4 of cannular configuration which can be exactly positioned with the aid of the centering bolt 10 without there being the risk of slipping of the drilling tool. The drilling tool 4 is provided with a bore 14 extending coaxially to its longitudinal axis, the bore 14 being adapted to the diameter of the centering bolt 10 such that the drilling tool 4 can be placed, with a clearance, onto the centering bolt 10 and drill through the cement residue 2.

The coaxial bore 14 of the drilling tool 4 is open towards the proximal end to allow pressure compensation.

The bore 14 may further comprise a stop for the centering bolt 10, e. g. by formation of a shoulder, which defines the penetration depth of the drilling tool 4.

When the drilling tool 4 has drilled the bore 18 through the cement residue 2 and/or the medullary block, the extraction tool 6 can be placed onto the centering bolt 10 and inserted, with the aid of the centering bolt 10 acting as a guide, into the bore 18 down to the distal end of the cement residue 2 and/or the medullary block. The bore diameter of the bore 18 substantially corresponds to the core diameter of a male thread 20 at the distal end of the extraction tool 6.

Figure 7:
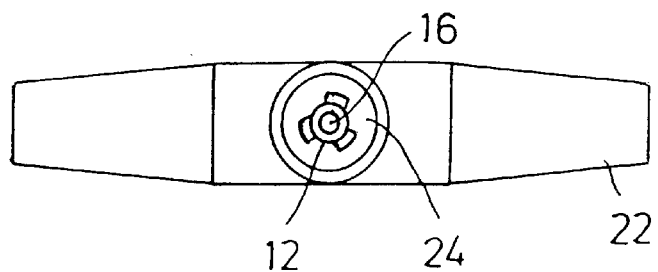
FIG. 7 shows a view of the drilling tool along line VII—VII of FIG. 6.
Figure 6:
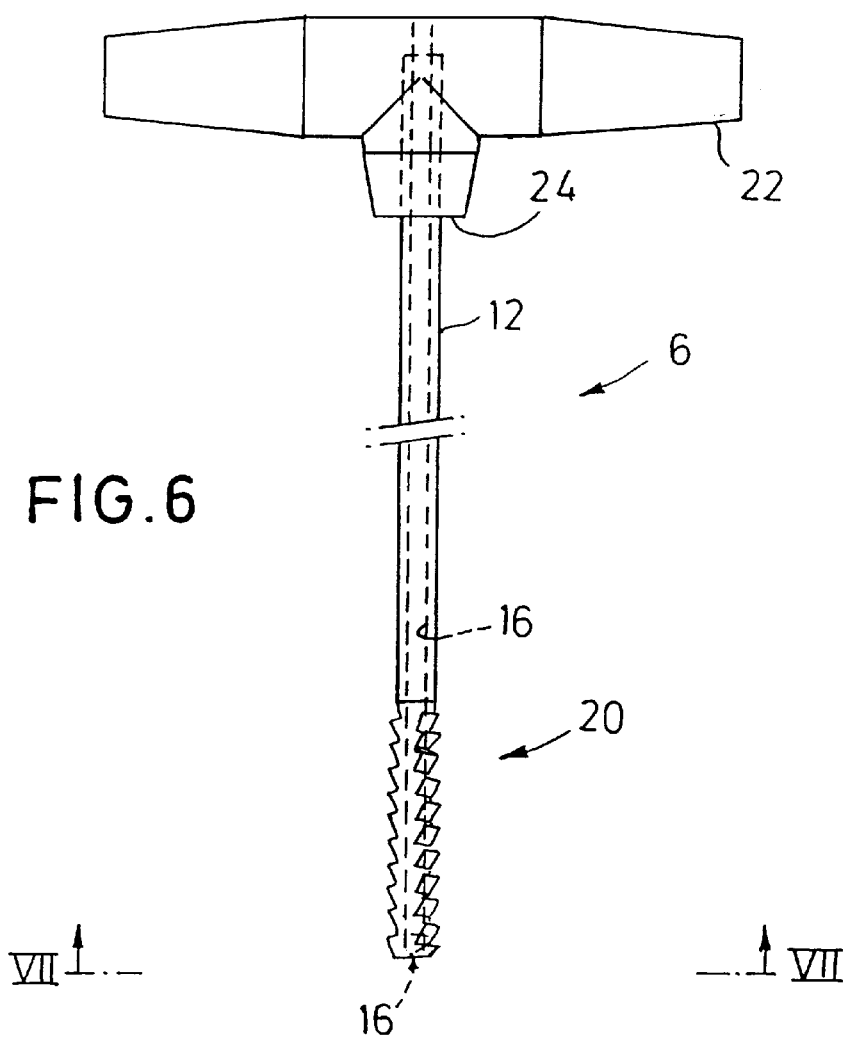
FIG. 6 shows a side view of the extraction tool.

Like the drilling tool 4 the extraction tool 6 is provided in its shaft 12 with a bore 16 extending coaxially to its longitudinal axis, the diameter of the bore 16 also being adapted to the diameter of the centering bolt 10 such that the extraction tool 6 can rotate, with a clearance, about the centering bolt 10. The extraction tool 6 is then anchored by the male thread 20 in a self-locking manner in the bore 18. The shaft of the extraction tool 6 has a length of e. g. 300 mm. The male thread 20 is configured as a cortex screw. As can best be seen in FIGS. 6 and 7, said male thread is cut free at locations offset from each other by 120°. The coaxial bore 16 is preferably of continuous configuration from the distal to the proximal end and extends through a grip 22 provided at the proximal end. At the lower portion of the grip an impact surface 24 is provided which is configured such that by means of forked hammers commonly used in the field of orthopaedics the extraction tool 6 with the distal cement residue 2 and/or the medullary block can be knocked out.

The coaxial bore 16, too, may be provided with a shoulder or a collar serving as a stop surface for the centering bolt 10 to define the penetration depth of the extraction tool 6.

If the coaxial bore 16 extends only in a distal section of the shaft 12, said bore 16 is connected with the outside via a radial duct extending through the shaft 12 to allow for pressure compensation.

Although a preferred embodiment of the invention has been specifically illustrated and described herein, it is to be understood that minor variations may be made in the apparatus without departing from the spirit and scope of the invention, as defined the appended claims.

What is claimed is:

1. A surgical instrument for removing at least one of a distal and peripheral cement (2) and a medullary block in a medullary cavity (8) when endoprostheses are replaced comprising a drilling tool (4) for drilling a bore through the cement and the medullary block and an extraction tool (6) for extracting the cement and the medullary block;

characterized in that the drilling tool (4) and the extraction tool (6) comprise a bore (14,16) extending coaxially to a tool shaft of the drilling tool (4) and the extraction tool (6) for receiving a centering bolt (10), the bore diameter of the coaxial bores (14,16) of the drilling tool (4) and the extraction tool (6) is substantially adapted to the centering bolt (10), and the centering bolt (10) being anchored at a predetermined location in the cement (2) and the medullary block in the medullary space (5) located distally there below and is configured as an axial guide for the drilling tool (4) or the extraction tool (6).

2. The surgical instrument according to claim 1, characterized in that the coaxial bores (14,16) of the drilling tool (4) and the extraction tool (6) are open at a proximal end thus forming a pressure compensation duct.

3. The surgical instrument according to claim 1, characterized in that the extraction tool (6) comprises a self-cutting male thread (20).

4. The surgical instrument according to claim 3, characterized in that the male thread (20) is configured as a cortex screw.

5. The surgical instrument according to claim 1, characterized in that the coaxial bores (14,16) for receiving the centering bolt (10) have a diameter ranging from 1.5 to 4 mm.

6. The surgical instrument according to claim 1, characterized in that the centering bolt (10) has a smaller diameter with respect to the bores (14,16) of the drilling tool (4) and the extraction tool (6).

7. The surgical instrument according to claim 1, characterized in that the distal ends of the bores (14,16) of the drilling tool (4) and the extraction tool (6) are flared towards the outside.

8. The surgical instrument according to claim 1, characterized in that the coaxial bores (14,16) in the drilling tool (4) and the extraction tool, respectively, comprise a stop for the centering bolt (10) to define the maximum penetration depth.

9. The surgical instrument according to claim 1, characterized in that the extraction tool (6) comprises a grip portion (22), and that on the bottom side of the grip portion (22) an impact surface (24) for a forked hammer is arranged.

10. A method for employing a surgical instrument for removing at least one of a distal and peripheral cement residue (2) and a medullary block in medullary cavities (8) when endoprostheses are replaced comprising a drilling tool (4) for drilling a bore through the cement and the medullary block and an extraction tool (6) for extracting the cement and the medullary block, characterized in that in a first step anchoring a centering bolt (10) at a predetermined location in the cement residue (2) and the medullary block in the medullary space (5) located distally there below, in a second step employing the centering bolt (10) as an axial guiding means for the drilling tool (4) having a coaxial bore (14) for receiving said centering bolt (10), and the drilling tool (4) produces a bore (18) extending through the cement residue (2) and the medullary block, in a third step inserting the extraction tool (6) having a coaxial bore (16) down to a distal end of the cement (2) or the medullary block into the bore (18) produced in the second step in the cement (2) or the medullary block by means of the drilling tool (4), wherein the centering bolt (10) is configured as a guiding means for the extraction tool (6), and in a fourth step extracting the cement residue (2) and the medullary block with the aid of the extraction tool (6).

* * * * *